(12) United States Patent
Peyman

(10) Patent No.: US 6,855,163 B2
(45) Date of Patent: Feb. 15, 2005

(54) GRADUAL CORRECTION OF CORNEAL REFRACTIVE ERROR USING MULTIPLE INLAYS

(75) Inventor: Gholam A. Peyman, New Orleans, LA (US)

(73) Assignee: Minu, LLC, Pittsboro, NC (US)

( * ) Notice: Subject to any disclaimer, the term of this patent is extended or adjusted under 35 U.S.C. 154(b) by 0 days.

(21) Appl. No.: 10/197,885

(22) Filed: Jul. 19, 2002

(65) Prior Publication Data

US 2004/0015234 A1 Jan. 22, 2004

(51) Int. Cl.⁷ .................................................. A61F 2/14
(52) U.S. Cl. ........................ 623/5.11; 623/5.12; 623/906
(58) Field of Search ........................ 623/4.1, 5.11–5.16, 623/6.32–6.34, 906

(56) References Cited

U.S. PATENT DOCUMENTS

| | | | |
|---|---|---|---|
| 4,624,669 A | * 11/1986 | Grendahl | 623/5 |
| 4,655,774 A | 4/1987 | Choyce | |
| 4,840,175 A | 6/1989 | Peyman | |
| 5,030,230 A | * 7/1991 | White | 623/5 |
| 5,139,518 A | * 8/1992 | White | 623/5 |
| 5,196,027 A | 3/1993 | Thompson et al. | |
| 5,405,384 A | 4/1995 | Silvestrini | |
| 5,693,092 A | * 12/1997 | Silvestrini et al. | 623/5 |
| 5,919,185 A | 7/1999 | Peyman | |
| 5,964,748 A | 10/1999 | Peyman | |
| 5,964,776 A | 10/1999 | Peyman | |
| 6,063,073 A | 5/2000 | Peyman | |
| 6,102,946 A | 8/2000 | Nigam | |
| 6,171,336 B1 | * 1/2001 | Sawusch | 623/5.11 |
| 6,197,019 B1 | 3/2001 | Peyman | |
| 6,217,571 B1 | 4/2001 | Peyman | |
| 6,221,067 B1 | 4/2001 | Peyman | |
| 6,228,113 B1 | * 5/2001 | Kaufman | 623/5.11 |
| 6,277,146 B1 | 8/2001 | Peyman et al. | |
| 6,280,471 B1 | 8/2001 | Peyman et al. | |
| 6,358,280 B1 | * 3/2002 | Herrick | 623/6.26 |
| 6,589,280 B1 | * 7/2003 | Koziol | 623/5.12 |
| 6,638,304 B2 | * 10/2003 | Azar | 623/6.22 |

* cited by examiner

*Primary Examiner*—Corrine McDermott
*Assistant Examiner*—Cheryl Miler
(74) *Attorney, Agent, or Firm*—Bell, Boyd & Lloyd LLC (57) ABSTRACT

A system adapted to modify refractivity of a cornea of an eye, including a first component, and adapted to be implanted at a first depth in the cornea. A second component, separate from the first component, is adapted to be implanted at a second depth in the cornea at a position relative to the first component, such that an axis passing through the eye parallel to the optical axis passes through the second component without passing through the first component. The second depth is closer to the front surface of the cornea than is the first depth.

84 Claims, 3 Drawing Sheets

GRADUAL CORRECTION OF CORNEAL REFRACTIVE ERROR USING MULTIPLE INLAYS

FIELD OF THE INVENTION

The present invention relates to a method and apparatus for changing the refractive properties of the cornea by implanting multiple inlays in the cornea. More particularly, the present invention relates to a system and method for changing the refractive properties of the cornea by implanting two inlays at different depths in the cornea and at different lateral positions with respect to the optical axes.

BACKGROUND OF THE INVENTION

A conventional method for correcting the refractive error in a cornea is keratophakia, i.e., implantation of a lens inside the cornea. Keratophakia uses an implant, which is placed into the cornea approximately equidistant from the exterior surface of the cornea and the interior surface. The procedure is usually done by first preparing a lens from corneal donor tissue or synthetic material using a cryo-lathe. The lens is implanted by removing a portion of the cornea with a device called a microkeratome, and the tissue is sutured back into place over the lens. However, there can be problems when microkeratomies are used for cutting the cornea. First, irregular keratectomies or perforations of the eye can result. Second, the recovery of vision can be rather prolonged.

Another surgical technique exists that uses a femtosecond laser to separate layers inside the stroma at least two-thirds of the distance from the top surface of the cornea to the inside of the eye. An incision is made to access this area and a solid inlay is inserted to help correct myopia in the eye. However, by separating the layers in the bottom two-thirds of the stroma, it is difficult to access the separated area to insert the inlay and virtually impossible to change or modify the inlay without another extensive surgical procedure. This procedure also requires making an incision, which is parallel to the visual axis and is limited in the lateral direction by a maximum size of 0.3 mm, to encase a relatively rigid inlay that forces the tissue in the lateral direction.

Additional surgical techniques exist that use ultraviolet light and short wavelength lasers to modify the shape of the cornea. For example, excimer lasers, such as those described in U.S. Pat. No. 4,840,175 to Peyman, which emit pulsed ultraviolet radiation, can be used to decompose or photoablate tissue in the live cornea so as to reshape the cornea. The entire content of U.S. Pat. No. 4,840,175 is incorporated by reference herein.

Specifically, the Peyman patent discloses the laser surgical technique known as laser in situ keratomycosis (LASIK). In this technique, a portion of the front of the live cornea can be cut away in the form of a flap having a thickness of about 160 microns. This cut portion is removed or drawn back from the live cornea to expose an inner surface of the cornea. A laser beam is then directed onto the exposed inner surface to ablate a desired amount of the inner surface up to 150–180 microns deep. The cut portion is reattached over the ablated portion of the cornea and assumes a shape conforming to that of the ablated portion. Additionally, in the LASIK procedure, a femtosecond laser can be used to cut and separate the flap.

However, because only a certain amount of cornea can be ablated without the remaining cornea becoming unstable or experiencing outbulging (eklasisa), this technique may not be especially effective in correcting very high myopia. That is, a typical cornea is on average about 500 microns thick. The laser ablation technique generally requires that at least about 250 microns of the corneal stroma remain after the ablation is completed so that instability and outbulging do not occur.

Additional methods for correcting the refractive error in the eye include inserting an implant between layers of the cornea. Generally, this is achieved using several different methods. One method involves inserting a ring between layers of the cornea, as described in U.S. Pat. No. 5,405,384 to Silvestrini. Typically, a dissector is inserted in the cornea and forms a channel therein. Once it is removed, a ring is then inserted into the channel to alter the curvature of the cornea. In another method, a flap can be created in a manner similar to the LASIK procedure, and a lens can be inserted under the flap, as described in U.S. Pat. No. 6,102,946 to Nigam. A further method involves forming a pocket using an instrument, and inserting an implant into the pocket, as described in U.S. Pat. No. 4,655,774 to Choyce. The entire contents of U.S. Pat. Nos. 4,655,774, 5,405,384 and 6,102,946 are incorporated by reference herein.

However, with the above-described techniques, a knife or other mechanical instrument is generally used to form the channel, flap or pocket. Use of these instruments may result in damage or imprecision in the cut or formation of the desired area in which the implant is placed.

Another method for correcting the vision in the eye includes removing the epithelial cells from the surface of the cornea, as described in U.S. Pat. No. 5,196,027 to Thompson et al. A synthetic lens is secured over the central corneal region, and which is ablated using a laser. Pharmacological agents may then be applied to the surface of the lens to enhance regrowth of the epithelial cells over the lens.

However, the procedure described in the Thompson et al. patent generally requires an adhesive or glue to hold the lens in position, along with peripheral groove formed in the surface of the cornea, into which a portion of the lens is positioned. Gluing the lens to the cornea, not only can result in some loss of the lens transparency to the media, but it also results in a lens that, if removed, would likely result in scaring of the cornea. Further scaring can result from the peripheral groove formed in the surface of the cornea. Additionally, in the Thompson et al. procedure, the removed epithelial cells are discarded, which can significantly delay wound healing. Furthermore, Thompson teaches using only one lens for implantation in the eye. This can potentially increase the thickness of the required lens, and thus inhibit the flow of nutrients through the lens.

Therefore, there exists a need for an improved method and system for correcting the refractive error in the cornea of an eye.

SUMMARY OF THE INVENTION

Accordingly, it is an object of the present invention to provide an improved method and system for correcting the refractive error in the cornea of an eye.

It is another object of the present invention to provide a system and method for implantation of an intracorneal inlay that does not delay wound healing.

It is still another object of the present invention to provide a system and method for implantation of an intracorneal inlay that reduces the potential for scaring of the cornea.

It is yet another object of the present invention to provide a system and method for implantation of an intracorneal inlay that can be removed and/or replaced without damaging the cornea.

It is still yet another object of the present invention to provide a system and method for implantation of multiple intracorneal inlays that reduce the inhibition of the flow of nutrients through the inlay.

The foregoing objects are basically attained by a system and adapted to modify refractivity of a cornea of an eye, including a first component, and adapted to be implanted at a first depth in the cornea. A second component, separate from the first component, is adapted to be implanted at a second depth in the cornea at a position relative to the first component, such that an axis passing through the eye parallel to the optical axis passes through the second component without passing through the first component. The second depth is closer to the front surface of the cornea than is the first depth.

The foregoing objects are further attained by a system and method adapted to modify refractivity of a cornea of an eye, including a first component having an opening therein, adapted to be implanted in the cornea such that the optical axis of the eye passes through the opening and a second component, adapted to be implanted in the cornea such that a portion of the second component is closer to the optical axis than a portion of the first component.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure.

DETAILED DESCRIPTION OF THE INVENTION

As initially shown in FIGS. 1–17, the refractive properties of eye 10 can be altered using laser 12 to separate an inner portion of the cornea 14 into first internal corneal surface 16 and second internal corneal surface 18. This separation creates an internal corneal flap 20 in the cornea 14, under which a first component or intracorneal inlay 22 can be placed. Additionally, as discussed in more detail below, a second flap 24 can be formed in the surface of the cornea, and a second separate component or intracorneal inlay 26 can be inserted under the second flap (see FIGS. 7–17). Each inlay itself changes the shape of the cornea and thus the refractive properties thereof, and thus by inserting either or both inlays, it is possible to correct myopia, hyperopia and/or astigmatism.

To begin, the refractive error in the eye is measured using wavefront technology, as is known to one of ordinary skill in the art. The refractive error measurements are transmitted to a computerized lathe (not shown) or other lens-shaping machine, where the shape of intracorneal inlay 22 is determined using the information from the wavefront device. Alternatively, the intracorneal inlay 22 can be manufactured or shaped prior to the use of the wavefront technology and can be stored in a sterilized manner until that specific shape or size is needed.

Intracorneal inlay 22 is preferably any polymer having about 50% water content; however, the water content can be any percentage desired. The lens may be formed from synthetic or organic material or a combination thereof. For example, the lens can be collagen combined with or without cells; a mixture of synthetic material and corneal stromal cells; silicone or silicone mixed with collagen; methyl-metacrylate; any transparent material, such as polyprolidine, polyvinylpylidine, polyethylenoxyde, etc.; or any deformable polymer, which can change its shape with ablation after implantation, such as methacrylate and acrylic acid gel.

Figure 4:
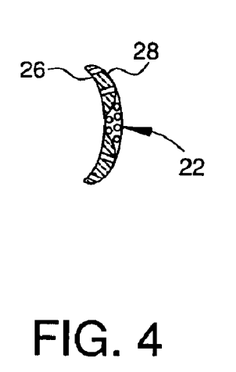
FIG. 4 is a side elevational view in cross-section of the inlay in FIG. 3, taken along lines 4—4.

As shown in FIG. 4, intracorneal inlay 22 has a first surface 26 and a second surface 28 and is porous to allow oxygen and nutrients to pass therethrough. Generally, intracorneal inlay 22 is preferably about 0.5 mm to 10 mm wide. The thickness is preferably about 5–2000 microns, and more preferably less than 200 microns. The inside edge can be thinner or thicker than the outside edge; for example, the inside edge can have a thickness of about 1–100 microns, while the outside edge has a thickness of about 20–3000 microns. However, the intracorneal inlay 22 can have any thickness or configuration that would allow it to elevate or move any portion of surface 16 relative to surface 18. The thickness and position of intracorneal inlay 22 generally defines the degree of correction of the cornea.

Preferably, inlay 22 is formed from an ablatable polymer and has at least one and more preferably several hundred physical openings or microperforations 23 formed as passageways from the first surface of the inlay through the inlay to the second surface of the inlay. Each microperforation is about 0.1 microns to about 500 micros in diameter and extends from the first surface 26 to the second surface 28. These perforations form a net in the inlay, and permit molecules of oxygen, water, solute and protein to permeate through the inlay with substantially no or no inhibition. Any or all of the microperforations or openings in the any of the inlays described herein can have a glare-free material disposed thereon, if desired. For a further discussion of glare-free material, refer to U.S. Pat. Nos. 6,280,471 and 6,277,146 both to Peyman et al., the entire contents of both of which are incorporated herein by reference.

Figure 3:
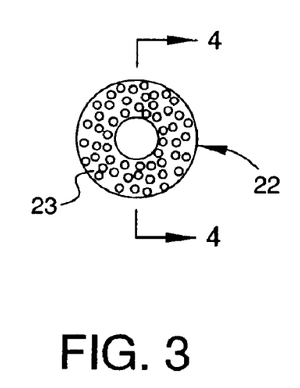
FIG. 3 is a top plan view of a intracorneal inlay according to a preferred embodiment of the present invention.

As seen in FIGS. 3 and 4, intracorneal inlay 22 is preferably substantially ring-shaped; but can be a circular or semicircular inlay. For example, intracorneal inlay 22 can have a split or have multiple portions that couple or fit together, it can be flat, arcuate, or tapered edges. Additionally, intracorneal inlay 22 may have any combination of these properties. Intracorneal inlay 22 can have multiple portions that can couple together, simply abut one another, they can lay near each other, not necessarily touching each other or the inlay portions can be separated from each other. Intracorneal inlay 22 can have multiple layers on top of each other, or have two sides with different thickness, which would help to correct astigmatism.

Additionally, the intracorneal inlay 22 preferably allows light in the visible spectrum to pass therethrough. The intracorneal inlay 22 can have refractive properties itself, and can have different or similar refractive properties to the refractive properties of the cornea. The inlay can have pigmentation added thereto to change the color of the intracorneal inlay 22 or it can be photochromatic. Furthermore, it is not necessary for the intracorneal inlay 22 to have a hole or aperture therethrough. The intracorneal inlay 22 can have a substantially planer surface or an arcuate surface with no holes or apertures therein. For additional configurations of inlays, see U.S. Pat. Nos. 6,063,073 and 6,217,571 both to Peyman, the entire contents of both of which are herein incorporated by reference.

Figure 1:
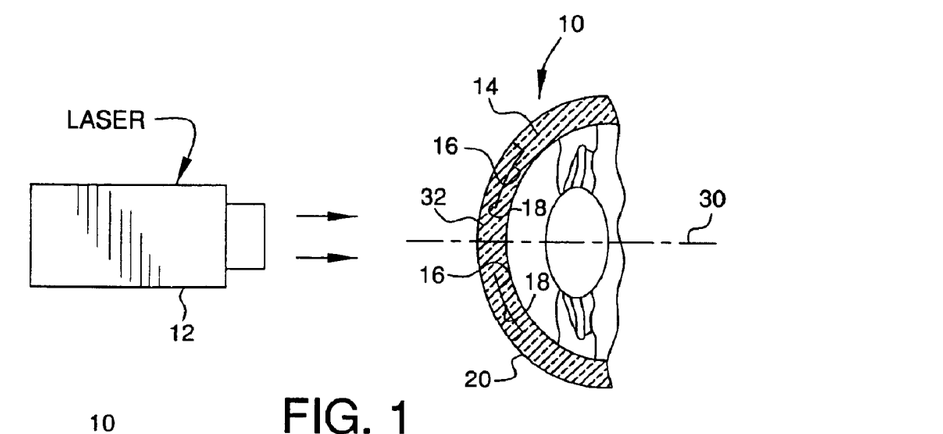
FIG. 1 illustrates a method of forming a flap in the cornea of an eye, by irradiating the cornea with a laser.

As seen specifically in FIG. 1, a flap 20 is formed in the surface of the cornea. The flap can be formed using a laser, or it can be formed using a microkeratome as disclosed in U.S. Pat. No. 5,964,776 to Peyman, the entire contents of which are herein incorporated by reference. When a laser is used, the laser 12 is aimed at the surface of the cornea of the eye and when activated, the laser preferably separates the internal area of the cornea offset from the main optical or visual axis 30 into a first substantially ring-shaped internal surface 16 and a second substantially ring-shaped internal surface 18 to form the substantially circular or ring-shaped corneal flap 20. First internal surface 16 faces in a posterior direction of cornea 14 and the second internal surface 18 faces in an anterior direction of the cornea 14. The flap 20 preferably has a uniform thickness of about 10–250 microns, and more preferably about 80–100 microns, but can be any suitable thickness. A portion 32 of flap 20 preferably remains attached to the cornea by an area located at the main optical axis 30. However, the laser can form a flap of any suitable configuration, such a flap attached to the cornea at a location other than at the main optical axis or a flap that is not attached to the cornea at all. Additionally, the flap may be shaped or sized as desired and does not need to be circular or ring-shaped.

Laser 12 preferably is an ultrashort pulse laser, such as a femto, pico, or attosecond laser; but may be any light emitting device suitable for creating a flap in the cornea as described above. The ultrashort pulse laser is positioned in front of the eye and focuses the laser beam in the cornea at the desired depth and in the desired flap configuration. Ultrashort pulse lasers are desired since they are high precision lasers that require less energy than conventional lasers to cut tissue and do not create "shock waves" that can damage surrounding structures. Cuts made by ultrashort pulse lasers can have very high surface quality with accuracy better than 10 microns, resulting in more precise cuts than those made with mechanical devices or other lasers. This type of accuracy results in less risks and complications than the procedures using other lasers or mechanical devices.

However, it is noted that the flap 20 can be formed by any manner or device desired. For example, the flap can be formed using any suitable laser, a microkerotome or a knife, as is known in the art.

Figure 2:
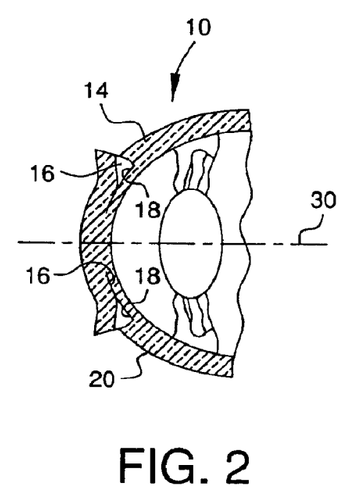
FIG. 2 is a side elevational view in cross-section of the eye of FIG. 1, with a ring-shaped flap formed in the surface of the cornea.
Figure 5:
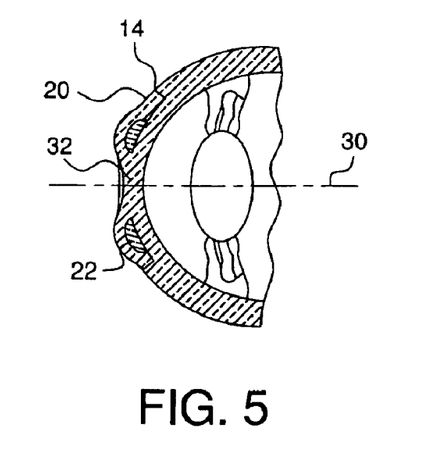
FIG. 5 is a side elevational view in cross-section of the eye of FIG. 2, with the lens of FIG. 3 inserted under the flap.

As seen in FIG. 2, the flap 20 is then lifted using any device known in the art, such as spatula or microforceps or any other device, and intracorneal inlay 22 is positioned or introduced around or at least partially encircling the main optical axis 30 and between the first internal surface 16 and second internal surface 18 of the flap 20. However, as stated above, the flap does not necessarily have to be attached at the main optical axis, and in such a case intracorneal inlay 22 is merely placed under the flap. The flap 20 is then replaced so that it covers or lies over the intracorneal inlay 22 in a relaxed state, as seen in FIG. 5. In other words, intracorneal inlay 22 does not force flap 20 away from the internal surface 18 and therefore the refractive properties of the cornea are not altered due to a tension force being applied to the flap.

Once the flap is in place the refractive properties of the eye can be remeasured using wavefront technology, and it can be determined if any refractive error remains in the eye. Generally, the refractive error is less than ±2.0 diopters sphere or astigmatism.

Figure 6:
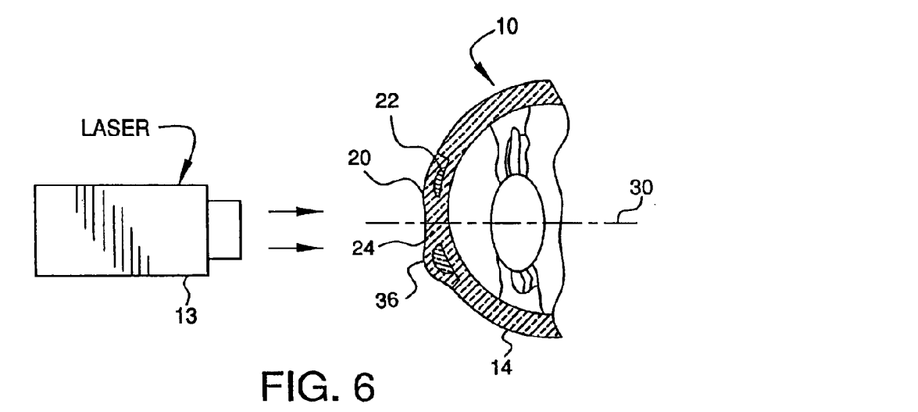
FIG. 6 is a side elevational view of the eye of FIG. 6, with the inlay being ablated by a laser.

If necessary, or desired, the inlay 22 can then be ablated by a laser beam that is activated outside the cornea and fired through the cornea to contact a portion of the inlay, as shown in FIG. 6, or the flap 20 can be moved to the side and the inlay can be ablated directly. Laser 13 can be an excimer laser, which are generally known in the art for being capable of ablating both corneal tissue and synthetic material. However, since excimer lasers are generally developed for ablation of the cornea, there are expensive to produce, require toxic fluorine gases, and are difficult to maintain. Therefore, it may be preferable to ablate the implant 22 using lasers that are cheaper and easier to maintain. Certain lasers that produce a wavelength of about 355 nm can be cheaper and easier to maintain. However, it is noted that the laser can emit a beam having a wavelength of about 193 nm to about 1300 nm.

Preferably, when using this type of laser, the implant is ablated, producing holes in the polymer, without producing a coagulative effect on the material. The 355 nm photon has three times the energy of the conventional 1064 nm photon, enabling the 355 photon to break molecular bonds. The 355 nm wavelength can be generated using a diode pumped solid-state (DPSS) Nd-YAG laser, which is double frequencied to 532 nm and mixed with a Nd-YAG at 1064 nm, producing the 355 nm wavelength.

Additionally, the combination of a diffraction-linked beam and a short wavelength laser can enable machining of the implant, since the focal spot size is proportional to the wavelength. For example, the laser can emit a short pulse or ultrashort pulse of a picosecond, a nanosecond, a femtosecond or an attosecond. However, the laser can be any suitable continuous or pulsed laser, or any laser that emits a beam in the infrared or visual spectrum.

Preferably, when utilizing this type of frequency laser, a flying spot laser is used, which can be moved though a software program across the inlay to ablate the desired portion of the implant.

To further correct the refractive error in the cornea, a second flap 24 can be formed from the corneal epithelium on the surface 36 of the cornea 14 and a second inlay 26 can be placed under the second flap, a seen in FIGS. 7–17. The second inlay can be positioned under the second flap, during the same procedure (i.e., within minutes or seconds of the previous inlay) or at a later date or time (e.g., hours, days, weeks, months, or years later). Preferably, the flap is formed overlying portion 32 using a using alcohol, enzymes, such as condrotinase, plamin, alpha-chemotrypsin, pepsin, trypsin, or any other suitable enzyme, a laser, such as an attosecond or femtosecond laser, a microkeratome or a knife.

Figure 7:
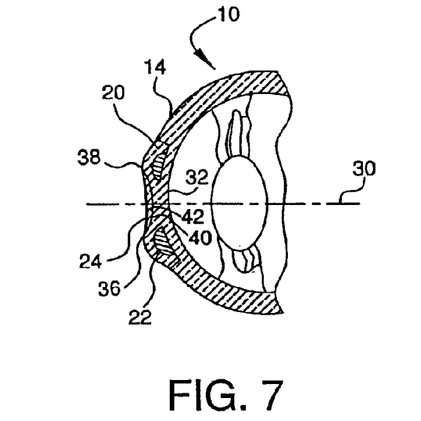
FIG. 7 is a side elevational view in cross-section of the eye of FIG. 5, with a second flap formed in the surface of the cornea.
Figure 8:
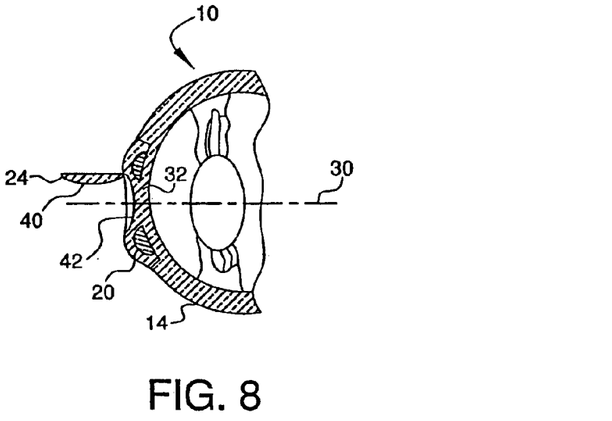
FIG. 8 is a side elevational view in cross-section of the eye of FIG. 6, with the second flap moved to expose a portion of the cornea.

When alcohol is used, the alcohol loosens the epithelium from the basement membrane, which allows removal of the epithelial layer. Heating the alcohol solution can also loosen the epithelium and facilitate removal. It is noted that any of the herein described solutions, such as the enzyme solutions can also be heated to facilitate removal of the epithelium. Preferably, the alcohol is heated to between about 40° C. and about 50° C., and more preferably to about 47° C. The flap can also be formed to remain at least partially attached to the cornea, as shown in FIGS. 7 and 8, by a portion 38, that allows the second flap to be positioned in the proper orientation, if it is desired to have flap repositioned over the second inlay 26. The flap has a first surface 40 and a second surface 42. The first surface 40 faces in a posterior direction of the eye the second surface faces in an anterior direction of the eye.

The second flap 24 is a relatively small flap that preferably at least partially overlies or is concentric about the visual axis or main optical axis 30 and can be attached to the cornea 14 by portion 38. However, the flap can be formed on any portion of the cornea desired and in any suitable manner, such as with a knife, blade or laser, as discussed above. It is noted that the location of the flap does not necessarily need to be concentric about the main optical axis and can be at any location on the surface of the eye and may be any size desired.

The flap is preferably pealed or moved away from the surface of the cornea using a suction device, microfoceps, or using any other device known in the art. For a further discussion of the formation of this type of flap, see U.S. patent application Ser. No. 09/843,141, filed Apr. 27, 2001, the entire contents of which are incorporated herein by reference.

Figure 9:
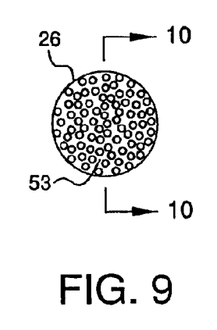
FIG. 9 is a top plan view of a second intracorneal inlay according to the preferred embodiment of the present invention.

Once the flap is moved to expose surfaces 40 and 42, second intracorneal inlay 26 can be positioned adjacent one of the surfaces. As shown in FIGS. 8 and 9, inlay 26 is a generally convex lens (for correction of hyperopia), with a first surface 44 and a second surface 46, and has a diameter that is smaller than the diameter of inlay 22; however, inlay 26 can be any suitable size or configuration desired. For example, inlay 26 can have a concave, convex-concave or piano-convex or torric surface, or any other configuration described above.

Inlay preferably is formed or a pliable material that conforms to the surface of the eye, and is ablatable by a laser, as described below; however, inlay 26 can be formed from any of the materials described above for inlay 22, or any other suitable material. For example, inlay 26 can be formed from any ablatable polymer, methacrolate and methocrolate gel, acrylic acid, polyvinylprolidine, silicone or a combination of the these materials or a combination of these materials with an organic material, such as collegen, chondrotine sulfate, glycosamine glycon, integrin, vitronectin, fibronnectine and/or mucopoly saccaride. Each of these materials and/or any combination thereof can also be used for inlay 22, described above. It should be noted that inlay 26 does not necessarily need to be positioned in the cornea after inlay 22 and can be positioned in the cornea prior to inlay 22.

Figure 10:
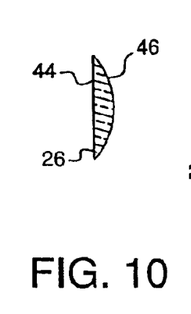
FIG. 10 is a side elevational view in cross-section of the inlay in FIG. 9, taken along lines 10—10.
Figure 11:
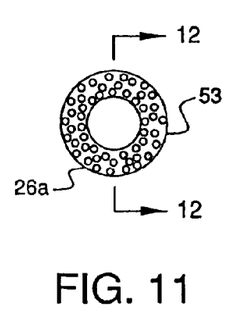
FIG. 11 is a top plan view of a third intracorneal inlay according to a second embodiment of the present invention.
Figure 12:
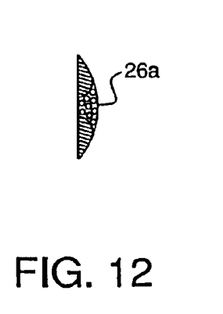
FIG. 12 is a side elevational view in cross-section of the inlay in FIG. 11, taken along lines 12—12.

Furthermore, as shown in FIGS. 10 and 11, inlay 26a has a first surface 44 and a second surface 46 and can be a substantially ring-shaped inlay (for the correction of myopia) and can be formed from any of the materials, have any of the configurations and/or dimensions of inlay 26.

Inlays 26 and 26a can have openings or microperforations 53 therein, which permit molecules of oxygen, water, solute and protein to permeate through the inlay with substantially no or no inhibition. Micro perforations 53 are substantially similar to micro perforations 23 and any description thereof is applicable to micro perforations 53.

Figure 13:
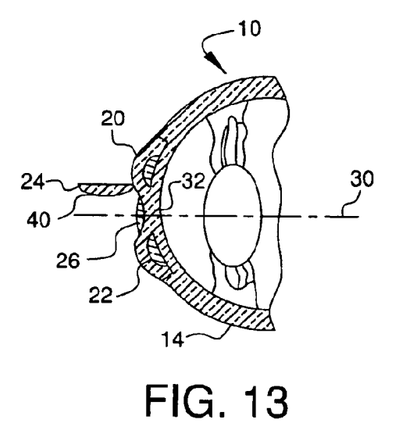
FIG. 13 is a side elevational view in cross-section of the eye of FIG. 8, with the intracorneal inlay of FIG. 9 inserted under the second corneal flap.
Figure 14:
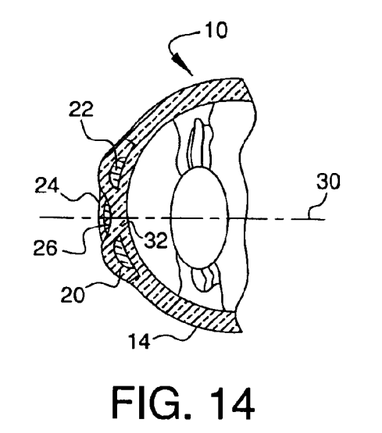
FIG. 14 is a side elevational view in cross-section of the eye of FIG. 13, with the second flap repositioned over the second intracorneal inlay.

As seen in FIGS. 13 and 14, intracorneal inlay 26 is preferably positioned closer to the surface of the cornea than intracorneal inlay 22. Additionally, since intracorneal inlay 26 has a diameter that is smaller than intracorneal inlay 22, and intracorneal inlay 22 preferably has an opening therein, an axis or line drawn substantially parallel the main optical axis through the second intracorneal inlay can pass through the opening of the first intracorneal inlay, and not pass through the inlay itself. However, as noted above, inlay 26 can have an opening therein, and in such a procedure the main optical axis of the eye can pass through the opening in each inlay.

Since each inlay has micro perforations, an excimer laser can be readily used to ablate the inlays, and will not cause irregularities in the surface. Each inlay is generally filled with water or glycosamine glycon from the cornea, which will leave similar ablation characteristics as the cornea. In addition, the spot size used for ablation will generally be larger than the diameter of each perforation, and therefore at least a portion of the inlay will be ablated. Furthermore, since the corneal epithelium cells are generally larger than the microperforations, the cornea epithelium will straddle the microperforation.

Figure 15:
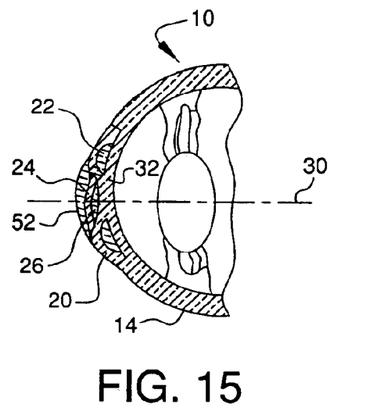
FIG. 15 is a side elevational view in cross-section of the eye of FIG. 14, with a contact lens placed on the surface of the cornea to aid in maintaining the second inlay stable.

After the procedure, a short-term bandage contact lens 52 may also be used to protect the cornea, and keep the second inlay stable, as seen in FIG. 15. Preferably, the contact covers the second inlay; however, the contact may be large enough to cover the area defined by each inlay and/or either or both flaps.

Figure 16:
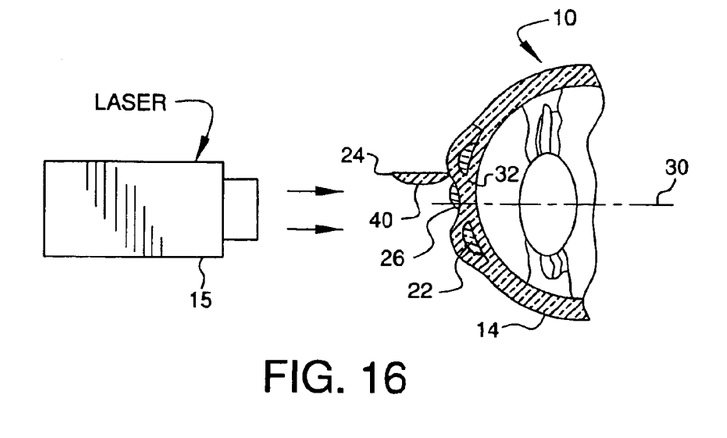
FIG. 16 is a side elevational view in cross-section of the eye of FIG. 13, with the second inlay being ablated by a laser.
Figure 17:
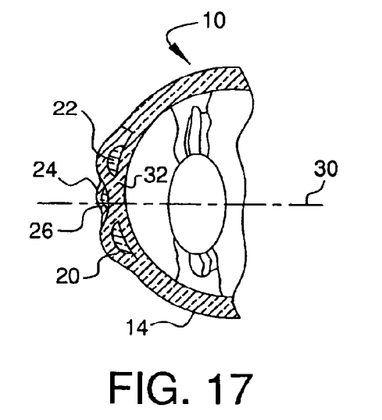
FIG. 17 is a side elevational view in cross-section of the eye of FIG. 16, with the second flap repositioned over the second ablated intracorneal inlay.

Additionally, as seen in FIGS. 16 and 17, if desired, second inlay 26 can be ablated with an excimer laser 15 or any other laser described above for the ablation of the first inlay 22. The flap is then positioned over the inlay (either ablated or unablated) without tension as described for flap 20, as seen in FIG. 17.

By performing the above described procedure using two separate components or inlays, the size or thickness of each inlay can be reduced, which reduces the inhibition of the flow of nutrients through the system in general.

Additionally, the refractive properties of the system can be adjusted after the procedure has been completed. For example, either or both of the inlays can be ablated using a laser after implantation. If desired, the flaps can be reopened and moved to expose the desired inlay, so that the inlay can be ablated directly, or the laser can ablate the inlay through the cornea epithelium. Furthermore, the refractive properties can be altered by replacement of one or both of the inlays. Since the adhesion between the inlays and cornea are not strong in the present procedures, one or both of the inlays can be readily replaced at anytime without the risk of a potential scar on the cornea.

While preferred embodiments have been chosen to illustrate the invention, it will be understood by those skilled in the art that various changes and modifications can be made therein without departing from the scope of the invention as defined in the appended claims.

What is claimed is:

1. A system, adapted to modify refractivity of a cornea of an eye, comprising:
   a first component, having an opening therein, and being adapted to be implanted at a first depth in the cornea without intersecting the optical axis of the eye; and
   a second component, having an opening therein, separate from said first component, and being adapted to be implanted at a second depth in the cornea, such that a front surface of said second component is closer to the front surface of the cornea than is a front surface of said first component implanted at said first depth, and at a position relative to said first component without contacting said first component, such that said second component substantially surrounds the optical axis of the eye when said second component is implanted at said second depth.

2. A system as claimed in claim 1, wherein:
   said first component is configured such that the optical axis of the eye passes through said opening when said first component is implanted at said first depth in the cornea.

3. A system as claimed in claim 1, wherein:
   said second component is configured such that the optical axis of the eye passes through said second component when said second component is implanted at said second depth in the cornea.

4. A system as claimed in claim 1, wherein:
   said first component is configured such that the optical axis of the eye passes through said opening when said first component is implanted at said first depth in the cornea; and
   said second component is configured such that the optical axis of the eye passes through said second component when said second component is implanted at said second depth in the cornea.

5. A system as claimed in claim 1, wherein:
   at least one of said first and second components includes a plurality of perforations therein.

6. A system as claimed in claim 5, wherein:
   at least one of said perforations has a cross-sectional dimension within a range of about 0.1 micron to about 500 microns.

7. A system as claimed in claim 1, wherein:
   at least one of said first and second components includes at least one of the following: collagen, acrylic acid, an ablatable polymer, methacrylate, methocrylate gel, polyvinylprolidine and silicone.

8. A system as claimed in claim 1, wherein:
   at least one of said first and second components is adapted for ablation by an energy source.

9. A system as claimed in claim 8, wherein:
   said energy source includes a laser.

10. A system as claimed in claim 1, wherein at least one of the following:
    said first component includes a first portion having a first refractive power; and
    said second component includes a second portion having a second refractive power.

11. A system as claimed in claim 1, wherein:
    said second component has an opening therein through which the optical axis passes when said second component is implanted at said second depth.

12. A system, adapted to modify refractivity of a cornea of an eye, comprising:
    a first component having an opening therein, adapted to be implanted at a first depth in the cornea such that the optical axis of the eye passes through said opening; and
    a second component having an opening therein, adapted to be implanted at a second depth in the cornea at a position relative to said first component without contacting said first component, such that a front surface of said second component is closer to the front surface of the cornea than is a front surface of said first component implanted at said first depth, and a portion of said second component is closer to the optical axis than a portion of said first component.

13. A system as claimed in claim 12, wherein:
    said second component is configured such that the optical axis of the eye passes through said opening when said second component is implanted at said second depth in the cornea.

14. A system as claimed in claim 12, wherein:
    said second component is configured such that the optical axis of the eye passes through said second component when said second component is implanted in the cornea.

15. A system as claimed in claim 12, wherein:
    at least one of said first and second components includes a plurality of perforations therein.

16. A system as claimed in claim 15, wherein:
    at least one of said perforations has a cross-sectional dimension within a range of about 0.1 micron to about 500 microns.

17. A system as claimed in claim 12, wherein: at least one of said first and second components includes at least one of the following: collagen, acrylic acid, an ablatable polymer, methacrylate, methocrylate gel, polyvinylprolidine and silicone.

18. A system as claimed in claim 12, wherein:
    at least one of said first and second components is adapted for ablation by an energy source.

19. A system as claimed in claim 18, wherein:
    said energy source includes a laser.

20. A system as claimed in claim 12, wherein at least one of the following:
    said first component includes a first portion having a first refractive power; and
    said second component includes a second portion having a second refractive power.

21. A system adapted to modify refractivity of a cornea of an eye, comprising:
    a first component, having an opening therein, and being adapted to be implanted at a first depth in the cornea without intersecting the optical axis of the eye; and
    a second component, separate from said first component, and being adapted to be implanted at a second depth in the cornea, such that a front surface of said second component is closer to the front surface of the cornea than is a front surface of said first component implanted at said first depth, and at a position relative to said first component without contacting said first component, such that said second component substantially surrounds the optical axis of the eye when said second component is implanted at said second depth, wherein at least one of said first and second components includes a plurality of perforations therein.

22. A system as claimed in claim 21 wherein:

said first component is configured such that the optical axis of the eye passes through said opening when said first component is implanted at said first depth in the cornea.

23. A system as claimed in claim 21, wherein:

said second component is configured such that the optical axis of the eye passes through said second component when said second component is implanted at said second depth in the cornea.

24. A system as claimed in claim 21, wherein:

said first component is configured such that the optical axis of the eye passes through said opening when said first component is implanted at said first depth in the cornea; and said second component is configured such that the optical axis of the eye passes through said second component when said second component is implanted at said second depth in the cornea.

25. A system as claimed in claim 21, wherein:

said second component has an opening therein.

26. A system as claimed in claim 21, wherein:

at least one of said perforations has a cross-sectional dimension within a range of about 0.1 micron to about 500 microns.

27. A system as claimed in claim 21, wherein:

at least one of said first and second components includes at least one of the following: collagen, acrylic acid, an ablatable polymer, methacrylate, methocrylate gel, polyvinylprolidine and silicone.

28. A system as claimed in claim 21, wherein:

at least one of said first and second components is adapted for ablation by an energy source.

29. A system as claimed in claim 28, wherein:

said energy source includes a laser.

30. A system as claimed in claim 21, wherein at least one of the following:

said first component includes a first portion having a first refractive power; and said second component includes a second portion having a second refractive power.

31. A system as claimed in claim 21, wherein:

said second component has an opening therein through which the optical axis passes when said second component is implanted at said second depth.

32. A system adapted to modify refractivity of a cornea of an eye, comprising:

a first component, having an opening therein, and being adapted to be implanted at a first depth in the cornea without intersecting the optical axis of the eye; and a second component, separate from said first component, and being adapted to be implanted at a second depth in the cornea, such that a front surface of said second component is closer to the front surface of the cornea than is a front surface of said first component implanted at said first depth, and at a position relative to said first component without contacting said first component, such that said second component substantially surrounds the optical axis of the eye when said second component is implanted at said second depth, wherein at least one of said first and second components includes at least one of the following: collagen, acrylic acid, an ablatable polymer, methacrylate, methocrylate gel, polyvinylprolidine and silicone.

33. A system as claimed in claim 32, wherein:

said first component is configured such that the optical axis of the eye passes through said opening when said first component is implanted at said first depth in the cornea.

34. A system as claimed in claim 32, wherein:

said second component is configured such that the optical axis of the eye passes through said second component when said second component is implanted at said second depth in the cornea.

35. A system as claimed in claim 32, wherein:

said first component is configured such that the optical axis of the eye passes through said opening when said first component is implanted at said first depth in the cornea; and said second component is configured such that the optical axis of the eye passes through said second component when said second component is implanted at said second depth in the cornea.

36. A system as claimed in claim 32, wherein:

said second component has an opening therein.

37. A system as claimed in claim 32, wherein:

at least one of said first and second components includes a plurality of perforations therein.

38. A system as claimed in claim 37, wherein:

at least one of said perforations has a cross-sectional dimension within a range of about 0.1 micron to about 500 microns.

39. A system as claimed in claim 32, wherein:

at least one of said first and second components is adapted for ablation by an energy source.

40. A system as claimed in claim 39, wherein:

said energy source includes a laser.

41. A system as claimed in claim 32, wherein at least one of the following:

said first component includes a first portion having a first refractive power; and said second component includes a second portion having a second refractive power.

42. A system as claimed in claim 32, wherein:

said second component has an opening therein through which the optical axis passes when said second component is implanted at said second depth.

43. A system adapted to modify refractivity of a cornea of an eye, comprising:

a first component having an opening therein, adapted to be implanted at a first depth in the cornea such that the optical axis of the eye passes through said opening; and a second component, adapted to be implanted at a second depth in the cornea at a position relative to said first component without contacting said first component, such that a front surface of said second component is closer to the front surface of the cornea than is a front surface of said first component implanted at said first depth, and a portion of said second component is closer to the optical axis than a portion of said first component, wherein at least one of said first and second components includes a plurality of perforations therein.

44. A system as claimed in claim 43, wherein:

said second component has an opening therein.

45. A system as claimed in claim 43, wherein:

said second component is configured such that the optical axis of the eye passes through said opening when said second component is implanted at said second depth in the cornea.

46. A system as claimed in claim 43, wherein:

said second component is configured such that the optical axis of the eye passes through said second component when said second component is implanted in the cornea.

47. A system as claimed in claim 43, wherein:

at least one of said perforations has a cross-sectional dimension within a range of about 0.1 micron to about 500 microns.

48. A system as claimed in claim 43, wherein:

at least one of said first and second components includes at least one of the following: collagen, acrylic acid, an ablatable polymer, methacrylate, methocrylate gel, polyvinylprolidine and silicone.

49. A system as claimed in claim 43, wherein:

at least one of said first and second components is adapted for ablation by an energy source.

50. A system as claimed in claim 49, wherein:

said energy source includes a laser.

51. A system as claimed in claim 43, wherein at least one of the following:

said first component includes a first portion having a first refractive power; and said second component includes a second portion having a second refractive power.

52. A system adapted to modify refractivity of a cornea of an eye, comprising:

a first component having an opening therein, adapted to be implanted at a first depth in the cornea such that the optical axis of the eye passes through said opening; and a second component, adapted to be implanted at a second depth in the cornea at a position relative to said first component without contacting said first component, such that a front surface of said second component is closer to the front surface of the cornea than is a front surface of said first component implanted at said first depth, and a portion of said second component is closer to the optical axis than a portion of said first component, wherein at least one of said first and second components includes at least one of the following: collagen, acrylic acid, an ablatable polymer, methacrylate, methocrylate gel, polyvinylprolidine and silicone.

53. A system as claimed in claim 52, wherein:

said second component has an opening therein.

54. A system as claimed in claim 52, wherein:

said second component is configured such that the optical axis of the eye passes through said opening when said second component is implanted at said second depth in the cornea.

55. A system as claimed in claim 52, wherein:

said second component is configured such that the optical axis of the eye passes through said second component when said second component is implanted in the cornea.

56. A system as claimed in claim 52, wherein:

at least one of said first and second components includes a plurality of perforations therein.

57. A system as claimed in claim 56, wherein:

at least one of said perforations has a cross-sectional dimension within a range of about 0.1 micron to about 500 microns.

58. A system as claimed in claim 52, wherein:

at least one of said first and second components is adapted for ablation by an energy source.

59. A system as claimed in claim 58, wherein:

said energy source includes a laser.

60. A system as claimed in claim 52, wherein at least one of the following:

said first component includes a first portion having a first refractive power; and said second component includes a second portion having a second refractive power.

61. A method for modifying refractivity of a cornea of an eye, comprising:

implanting a first component, having an opening therein, at a first depth in the cornea without intersecting the optical axis of the eye; and implanting a second component, separate from said first component, at a second depth in the cornea at a position relative to said first component without contacting said first component, such that a front surface of said second component is closer to the front surface of the cornea than is a front surface of said first component implanted at said first depth, and said second component substantially surrounds the optical axis of the eye when said second component is implanted at said second depth.

62. A method as claimed in claim 61, wherein:

said first component implanting step includes positioning said first component such that the optical axis of the eye passes through said opening when said first component is implanted at said first depth in the cornea.

63. A method as claimed in claim 61, wherein:

said second component implanting step includes positioning said second component such that the optical axis of the eye passes through said second component when said second component is implanted at said second depth in the cornea.

64. A method as claimed in claim 61, wherein:

said first component implanting step includes positioning said first component such that the optical axis of the eye passes through said opening when said first component is implanted at said first depth in the cornea; and said second component implanting step includes positioning said second component such that the optical axis of the eye passes through said second component when said second component is implanted at said second depth in the cornea.

65. A method as claimed in claim 61, wherein:

at least one of said first and second components includes a plurality of perforations therein.

66. A method as claimed in claim 65, wherein:

at least one of said perforations has a cross-sectional dimension within a range of about 0.1 micron to about 500 microns.

67. A method as claimed in claim 61, wherein:

at least one of said first and second components includes at least one of the following: collagen, acrylic acid, an ablatable polymer, methacrylate, methocrylate gel, polyvinylprolidine and silicone.

68. A method as claimed in claim 61, further comprising the step of:

ablating at least one of said first and second components using an energy source.

69. A method as claimed in claim 68, wherein:

said energy source includes a laser.

70. A method as claimed in claim 61, wherein at least one of the following:

said first component includes a first portion having a first refractive power; and said second component includes a second portion having a second refractive power.

71. A method as claimed in claim 61, wherein:

said second component has an opening therein.

72. A method as claimed in claim 71, wherein:

said second component implanting step includes positioning said second component such that the optical axis of the eye passes through said opening when said second component is implanted at said second depth in the cornea.

73. A method as claimed in claim 61, wherein:

said first and second component implanting steps position said first and second components such that a portion of the cornea is present between at least a portion of said first component and at least a portion of said second component.

74. A method for modifying refractivity of a cornea of an eye, comprising:

implanting a first component having an opening therein at a first depth in the cornea such that the optical axis of the eye passes through said opening; and implanting a second component at a second depth in the cornea at a position relative to said first component without contacting said first component, such that a front surface of said second component is closer to the front surface of the cornea than is a front surface of said first component implanted at said first depth, and a portion of said second component is closer to the optical axis than a portion of said first component.

75. A method as claimed in claim 74, wherein:

said second component implanting step includes positioning said second component such that the optical axis of the eye passes through said second component when said second component is implanted in the cornea.

76. A method as claimed in claim 74, wherein:

at least one of said first and second components includes a plurality of perforations therein.

77. A method as claimed in claim 76, wherein:

at least one of said perforations has a cross-sectional dimension within a range of about 0.1 micron to about 500 microns.

78. A method as claimed in claim 74, wherein:

at least one of said first and second components includes at least one of the following: collagen, acrylic acid, an ablatable polymer, methacrylate, methocrylate gel, polyvinylprolidine and silicone.

79. A method as claimed in claim 74, further comprising the step of:

ablating at least one of said first and second components using an energy source.

80. A method as claimed in claim 79, wherein:

said energy source includes a laser.

81. A method as claimed in claim 74, wherein at least one of the following:

said first component includes a first portion having a first refractive power; and said second component includes a second portion having a second refractive power.

82. A method as claimed in claim 74, wherein:

said second component has an opening therein.

83. A method as claimed in claim 82, wherein:

said second component implanting step includes positioning said second component such that the optical axis of the eye passes through said opening when said second component is implanted at said second depth in the cornea.

84. A method as claimed in claim 74, wherein:

said first and second component implanting steps position said first and second components such that a portion of the cornea is present between at least a portion of said first component and at least a portion of said second component.

* * * * *